United States Patent [19]

Chang et al.

[11] Patent Number: 4,476,322

[45] Date of Patent: Oct. 9, 1984

[54] SYNTHESIS OF DIMETHYLMETHYLENE DINITRAMINE

[75] Inventors: Marguerite S. Chang, Fort Washington; Robert R. Orndoff, Waldorf, both of Md.

[73] Assignee: The United States of America as represented by the Secretary of the Navy, Washington, D.C.

[21] Appl. No.: 394,218

[22] Filed: Jul. 1, 1982

[51] Int. Cl.³ .......................................... C07C 111/00
[52] U.S. Cl. ..................................... 564/109; 564/33; 564/107
[58] Field of Search ......................... 564/33, 107, 109

[56] References Cited

U.S. PATENT DOCUMENTS 2,856,429 10/1958 Saner .......................... 564/107 X Primary Examiner—Robert V. Hines
Attorney, Agent, or Firm—R. F. Beers; K. E. Walden; R. D. Johnson

[57] ABSTRACT

A process for preparing 2,4-dinitro-2,4-diazapentane by
(1) nitrating dimethylurea to form dimethyldinitrourea;
(2) hydrolyzing the dimethyldinitrourea to form methylnitramine;
(3) reacting one mole of methylamine with one mole of formaldehyde in aqueous solution to form 2-nitro-2-aza-1-propanol; and
(4) reaction one mole of methylnitramine with each mole of 2-nitro-2-aza-1-propanol to form one mole of 2,4-dinitro-2,4-diazapentane.

17 Claims, No Drawings

SYNTHESIS OF DIMETHYLMETHYLENE DINITRAMINE

BACKGROUND OF THE INVENTION

This invention relates to propellants and more particularly to energetic nitramine plasticizers for propellants.

In 1974 several energetic nitramines were disclosed as potentially useful as energetic plasticizers for propellants. 2,4-dinitro-2,4-diazapentane (commonly called dimethylmethylene dinitramine or DMMD) appeared to be the most promising of those candidates. However, its affect on the ballistic properties of a double base or composite propellant could not be evaluated because of the difficulty and costly process involved in preparing larger quantities of it. The literature procedure can be summarized as follows:

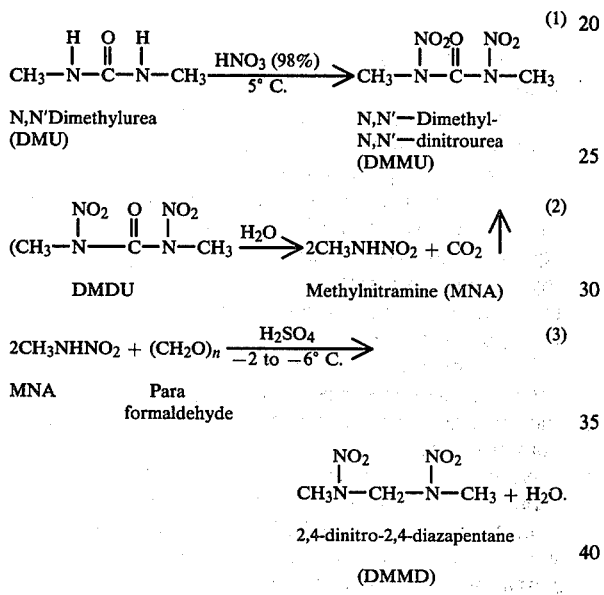

Kazuo Shiino and Senzo Oinuna, Kogyo Kayaku Kyokaishi 21, 351–7 (1960), disclose steps (1) and (2) of the process (see Chemical Abstracts volume 55, column 23340). The procedure requires the isolation and purification of N,N'-Dimethyl-N,N'-dinitrourea (DMDU) in step (1) prior to its hydrolysis in step (2). DMDU in isolated form is a unstable, energetic explosive (at least one accidental explosion has occurred). Additionally, the yield of DMDU is rather low. The hydrolysis of DMDU (step 2) is not reported in detail; however, of the isolation and purification of the product methylnitramine (MNA) is rather time consuming. Step (3) of the procedure was disclosed by Leon Goodman, in "Condensations of Primary Aliphatic Nitramines with Formaldehyde," J.A.C.S. 75, 3019 at 3020 (1953). Step 3, a condensation reaction between paraformaldehyde and 2 molecules of MNA, requires a huge excess of concentrated sulfuric acid (for depolymerization of paraformaldehyde and dehydrating of MNA) which is definitely impractical and economically not feasible for large-scale process.

SUMMARY OF THE INVENTION

Accordingly, one object of this invention is to provide an improved process for preparing 2,4-dinitro-2,4-diazapentane.

Another object of this invention is to provide a safer method of preparing 2,4-dinitro-2,4-diazapentane.

A further object of this invention is to provide a more economical method of preparing 2,4-dinitro-2,4-diazapentane.

Yet another object of this invention is to provide a large-scale process for preparing 2,4-dinitro-2,4-diazapentane.

These and other objects of this invention are accomplished by providing a process comprising the following steps in order:

(1) adding N,N'-dimethylurea in an organic solvent (e.g., methylene chloride) to mixed acid which is maintained at a temperature which is above the freezing point of mixed acid up to 5° C. to produce N,N'-dimethyl-N,N'-dinitrourea and then drowning the mixed acid solution in ice water;

(2) using an organic solvent to extract the N,N'-dimethyl-N,N'-dinitrourea from the mixed acid-water mixture;

(3) hydrolyzing the N,N'-dimethyl-N,N'-dinitrourea to form methylnitramine by adding the N,N'-dimethyl-N,N'-dinitrourea-organic solvent solution to water which is at a temperature of from 37° C. to 100° C.; and (4) isolating the product methylnitramine by:
  (a) evaporating the organic solvent phase to completion;
  (b) reducing the volume of the water phase by removing water to minimum until just before the methylnitramine begins to decompose;
  (c) extracting methylnitramine from the water phase with the organic solvent; and
  (d) evaporating the organic solvent to obtain methylnitramine;

(5) adding one mole of methylnitramine for each mole of formaldehyde to an aqueous solution of formaldehyde;

(6) allowing the methylnitramine to react with the aqueous formaldehyde to produce 2-nitro-2-aza-1-propanol;

(7) isolating the produce 2-nitro-2-aza-1-propanol from the reaction mixture;

(8) combining one mole of methylnitramine with each mole of 2-nitro-2-aza-1-propanol;

(9) slowly adding the mixture of methylnitramine and 2-nitro-2-aza-1-propanol to concentrated sulfuric acid which is maintained at a temperature of from just above the freezing point of concentrated sulfuric acid up to 5° C.; and

(10) isolating the product 2,4-dinitro-2,4-diazapentane.

2,4-dinitro-2,4-diazapentane is useful as an energetic ingredient or plasticizer in propellants and explosives.

DETAILED DESCRIPTION OF THE INVENTION

The process of the present invention may be summarized as follows:

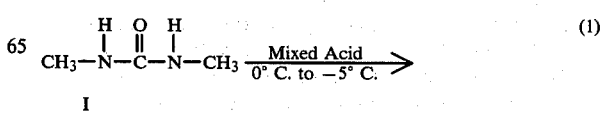

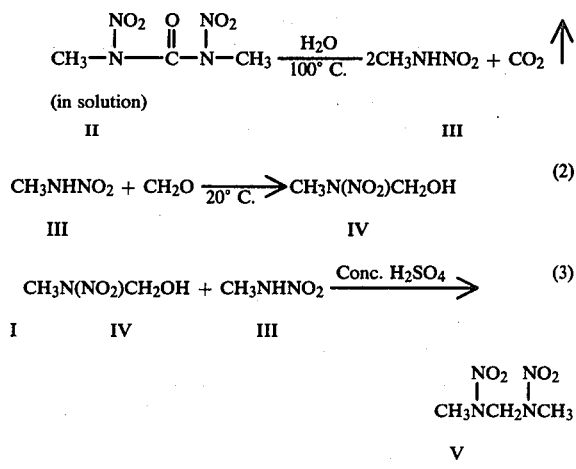

$$CH_3NHNO_2 + CH_2O \xrightarrow[20°C.]{} CH_3N(NO_2)CH_2OH \quad (2)$$

III IV $$CH_3N(NO_2)CH_2OH + CH_3NHNO_2 \xrightarrow{\text{Conc. } H_2SO_4} \quad (3)$$

I IV III $$\underset{V}{CH_3\overset{NO_2}{\overset{|}{N}}CH_2\overset{NO_2}{\overset{|}{N}}CH_3}$$

Step (1) comprises the nitration of N,N'-dimethylurea (I) using mixed acid to form N,N'-dimethyl-N,N'-dinitrourea (II) in solution followed by the hydrolysis of the N,N'-dimethyl-N,N'-dinitrourea to form methylnitramine (III).

A controlled addition of the N,N'-dimethylurea in an organic solvent such as methylene chloride, chloroform, 1,2-dichlorothane, or 1,1,2-trichloroethane is made to neat mixed acid which is the temperature range is determined by practical considerations such as the freezing point of mixed acid and the desired reaction speed. A preferred reaction temperature is from $-5°$ C. to $0°$ C. The reaction temperature is controlled by external cooling of the reaction mixture and by the slow, controlled addition of the N,N'-dimethylurea to the reaction mixture. The N,N'-dimethylurea is dissolved in an appropriate organic solvent prior to being added to the acid mixture (reaction mixture). The solvent must be (1) capable of holding both the N,N'-dimethylurea starting material and N,N'-dimethyl-N,N'-dinitrourea product in solution, (2) chemically inert to the mixed acid, and (3) essentially immiscible with the mixed acid. Suitable solvents include methylene chloride, chloroform, 1,2-dichloroethane, and 1,1,2-trichloroethane. Methylene chloride is the most preferred solvent. The examples provide guidance as to the amount of solvent to be used.

A mixed acid is an industry term which refers to any of the nitric acid/sulfuric acid mixtures which are used commercially to prepare nitroglycerin and other nitrate esters. Any of these mixed acid compositions which are used in the manufacture of nitroglycerin may be used in the nitration of N,N'-dimethylurea. A significant advantage of mixed acid is that it is inexpensive and widely available from commercial sources.

After completion of the nitration reaction, the reaction mixture is drowned in ice water. The organic solvent phase (layer) containing much of the product dimethyldinitrourea, is then separated from the mixed acid-water phase. More of the same organic solvent is then used in repeated extractions to remove more of the product N,N'-dimethyl-N,N'-dinitrourea from the mixed acid-water phase. The solution of N,N'-dimethyl-N,N'-dinitrourea in organic solvent is then treated (e.g., with 5% $Na_2CO_3$ in water) to remove traces of the acid.

Next, the N,N'-dimethyl-N,N'-dinitrourea is hydrolyzed to form methylnitramine. This can be conveniently done by adding the solution of methylnitramine in organic solvent to boiling or near boiling water (or more broadly to water at a temperature of from 37° to 100° C.). Because the product methylnitramine is soluble in water, very little water should be used. A preferred range for the molar ratio of N,N-'dimethyl-N,N'-dinitrourea to water is from 2:3 to 1:5. The hydrolysis converts the N,N'-dimethyl-N,N'-dinitrourea (II) into methylnitramine (III) according to

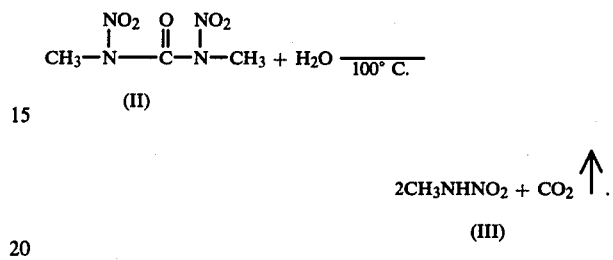

The organic solvent is evaporated from the aqueous phase.

A critical step in this process is the removal of as much water from the aqueous phase as is possible without decomposing methylnitramine. This may be done by conventional means such as evaporation. By doing this prior to extraction of the methylnitramine from the aqueous phase with organic solvents, the yield of methylnitramine is greatly increased. The reason for this is the greater solubility of methylnitramine in water than in organic solvents.

Next, the product methylnitramine is separated by extraction with the organic solvent (e.g., $CH_2Cl_2$) from the aqueous phase. The organic solvent fractions are combined and dried. The solvent is then evaporated, leaving an oily liquid from which the product methylnitramine (m.p. 49°–40° C.) is recrystallized.

In the next step, 1 mole of methylnitramine is reacted with 1 mole of formaldehyde to form 2-nitro-2-aza-1-propanol. An aqueous solution of formaldehyde is used; preferably the solution contains from 30 to 37 weight percent of formaldehyde. For convenience, the reaction may be run at ambient or room temperature (e.g., 20° to 25° C.). Next, the mixture is extraced with organic solvent to separate the product 2-nitro-2-aza-1-propanol.

An additional mole of methylnitramine is reacted with the 2-nitro-2-aza-1-propanol to produce 2,4-dinitro-2,4-diazapentane. The reactants (in approximately 1:1 molar ratio) are dissolved in a suitable organic solvent and the resulting solution is added to concentrated sulfuric acid at a controlled rate. The reaction temperature is maintained at a temperature above the freezing point of the concentrated sulfuric acid up to 5° C., but preferably from $-5°$ C. to $0°$ C. The product 2,4-dinitro-2,4-diazapentane is then isolated by extraction using a suitable organic solvent, washing to remove traces of the acid, evaporating off the solvent, and then recrystallizing the resulting solid. A suitable organic solvent is one that (1) is capable of holding the methylnitramine and 2-nitro-2-aza-1-propanol starting materials and the 2,4-dinitro-2,4-diazapentane product in solution, (2) chemically inert to concentrated sulfuric acid, and (3) essentially immiscible with concentrated sulfuric acid. Suitable solvents include methylene chloride, chloroform, 1,2-dichloroethane, and 1,1,2-trichloroethane. Methylene chloride is the most preferred solvent.

The general nature of the invention having been set forth, the following examples are presented as specific illustrations thereof. It will be understood that the invention is not limited to these examples but is susceptible to various modifications that will be recognized by one of ordinary skill in the art.

EXAMPLE 1

Preparation of methylnitramine

A solution of 100 g of N,N'-dimethylurea (DMU) in 200 ml of $CH_2Cl_2$ was slowly added to 312 ml of stirred mixed acid (56 parts by weight of nitric acid/47 parts by weight of sulfuric acid) which had previously been cooled to $-5°$ C. The temperature of the reaction mixture was kept at from $-5°$ C. to $0°$ C. through the controlled addition and external cooling. After the addition was completed, the reaction mixture was poured into a large excess of ice water. Following separation of the $CH_2Cl_2$ layer, the water phase was repeatedly extracted with $CH_2Cl_2$ to remove the remaining N,N'-dimethyl-N,N'-dinitrourea. All the methylene chloride fractions were then combined and twice washed with 5% aqueous sodium carbonate and then twice washed with distilled water.

The methylene chloride solution of N,N'-dimethyl-N,N'-dinitrourea was then added dropwise to 200 ml of boiling water; the water temperature was maintained at the boiling point during the entire addition and for an additional 20 minutes after the addition was completed. The volume of the aqueous phase was reduced by evaporating water until just before the methylnitramine began to decompose. The resulting aqueous solution was then cooled to room temperature and then repeatedly extracted with methylene chloride. The methylene chloride fractions were combined and then dryed with $MgSO_4$. The methylene chloride was then evaporated off, leaving an oily liquid (100 g, 98% yield) which was then precipitated from ether/hexane as solid crystals of methylnitramine (m.p. $39°$–$40°$ C.).

EXAMPLE 2

Preparation of 2-nitro-2-aza-1-propanol

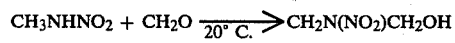

$$CH_3NHNO_2 + CH_2O \xrightarrow{20° C.} CH_2N(NO_2)CH_2OH$$

60.8 grams of the methylnitramine produced in Example 1 was added to 101 ml of 37% formaldehyde. The mixture was stirred one hour at $20°$ C. The product 2-nitro-2-aza-1-propanol was extracted from the mixture with methylene chloride ($3 \times 100$ ml). The methylene chloride fractions were combined, dried with magnesium sulfate ($MgSO_4$), and filtered to remove the magnesium sulfate.

EXAMPLE 3

Preparation of 2,4-dinitro-2,4-diazapentane

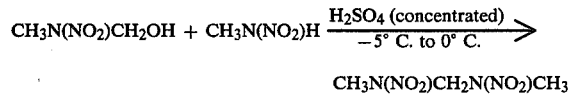

$$CH_3N(NO_2)CH_2OH + CH_3N(NO_2)H \xrightarrow[-5° C. \text{ to } 0° C.]{H_2SO_4 \text{ (concentrated)}}$$

$$CH_3N(NO_2)CH_2N(NO_2)CH_3$$

The solution of 2-nitro-2-aza-1-propanol in methylene chloride produced in Example 2 was combined with an additional 56 grams of methylnitramine. This mixture was slowly added to 300 ml of stirred concentrated sulfuric acid which had previously been cooled to $-5°$ C. to $-10°$ C. The temperature of the reaction mixture was kept at from $0°$ C. to $-5°$ C. throughout the controlled addition. After the addition was completed, the mixture was poured into a large excess of ice water. Following the separation of the methylene chloride phase, the water phase was repeatedly extracted with methylene chloride. All the methylene chloride fractions were then combined, twice washed with water, and then dried with magnesium sulfate. The magnesium sulfate was filtered out and then the methylene chloride was removed by evaporation under vacuum, leaving an oily liquid. The oily liquid was converted into solid white crystals of 2,4-dinitro-2,4-diazapentane (m.p. $56°$ C., 65 grams pure) by precipitation from a chloroform/hexane solvent mixture.

| Anld. Calcd. $C_3H_3N_4O_4$ | Found $C_3H_8N_4O_4$ |
|---|---|
| C 21.95 | C 21.89; 22.00 |
| H 4.89 | H 4.86; 4.93 |
| N 34.15 | N 34.13; 33.92 |

Obviously numerous modifications and variations of the present invention are possible in light of the above teachings. It is therefore understood that within the scope of the appended claims the invention may be practiced otherwise than as specifically described herein.

What is claimed as new and desired to be secured by Letters Patent of the United States is:

1. A process for preparing methylnitramine comprising the following steps in order:
   (1) adding N,N'-dimethylurea on an organic solvent to mixed acid which is maintained at a temperature which is above the freezing point of mixed acid up to $5°$ C. to produce N,N'-dimethyl-N,N'-dinitrourea and then drowning the mixed acid in ice water;
   (2) using an organic solvent to extract the N,N'-dimethyl-N,N'-dinitrourea from the mixed acid-water mixture;
   (3) hydrolyzing the N,N'-dimethyl-N,N'-dinitrourea to form methylnitramine by adding the N,N'-dimethyl-N,N'-dinitrourea—organic solvent solution to water which is at a temperature of from $37°$ C. to $100°$ C.; and
   (4) isolating the product methylnitramine by:
      (a) evaporating the organic solvent to completion;
      (b) reducing the volume of the water phase by removing water to a minimum until just before methylnitramine begins to decompose;
      (c) extracting methylnitramine from the water phase with the organic solvent; and
      (d) evaporating the organic solvent to obtain methylnitramine.

2. The process of claim 1 wherein step (1) is performed at a temperature of from $-5°$ C. to $0°$ C.

3. The process of claim 1 wherein boiling water is used in step (3).

4. The process of claim 1 wherein the molar ratio of N,N'-dimethyl-N,N'-dinitrourea to water in step (3) is from 2:3 to 1:5.

5. The process of claim 1 wherein the organic solvent is selected from the group consisting of methylene chloride, chloroform, 1,2-dichloroethane, 1,1,2-trichloroethane, and mixture thereof.

6. The process of claim 5 wherein the organic solvent is methylene chloride.

7. A process for preparing 2,4-dinitro-2,4-diazapentane from methylnitramine and aqueous formaldehyde comprising the following steps in order:
   (1) adding one mole of methylnitramine for each mole of formaldehyde to an aqueous solution of formaldehyde;
   (2) allowing the methylnitramine to react with the formaldehyde to produce 2-nitro-2-aza-1-propanol;
   (3) isolating the product 2-nitro-2-aza-propanol from the reaction mixture;
   (4) combining one mole of methylnitramine with each mole of 2-nitro-2-aza-1-propanol;
   (5) slowly adding the mixture of methylnitramine and 2-nitro-2-aza-1-propanol to concentrated sulfuric acid which is maintained at a temperature of from just above the freezing point of concentrated sulfuric acid up to 5° C.; and
   (6) isolating the product 2,4-dinitro-2,4-diazapentane.

8. The process of claim 7 wherein the aqueous formaldehyde solution comprises from about 30 to about 37 weight percent of formaldehyde.

9. The process of claim 7 wherein the concentrated sulfuric acid in step (5) is maintained at a temperature of from −5° C. to 0° C.

10. A process for preparing 2,4-dinitro-2,4-diazapentane comprising the following steps in order:
    (1) adding N,N'-dimethylurea in an organic solvent to mixed acid which is maintained at a temperature which is above the freezing point of mixed acid up to 5° C. to produce N,N'-dimethyl-N,N'-dinitrourea and then drowning the mixed acid solution in ice water;
    (2) using an organic solvent to extract the N,N'-dimethyl-N,N'-dinitrourea from the mixed acid-water;
    (3) hydrolyzing the N,N'-dimethyl-N,N'-dinitrourea to form methylnitramine by adding the N,N'-dimethyl-N,N'-dinitrourea-organic solvent solution to water which is at a temperature of from 37° C. to 100° C.;
    (4) isolating the product methylnitramine by:
       evaporating the organic solvent phase to completion;
       (b) reducing the volume of the water phase by removing water to a minimum until just before the methylnitramine begins to decompose;
       (c) extracting methylnitroamine from the water phase with the organic solvent; and
       (d) evaporating the organic solvent to obtain methylnitramine
    (5) adding one mole of methylnitramine for each mole of formaldehyde to an aqueous solution of formaldehyde;
    (6) allowing the methylnitramine to react with the formaldehyde to produce 2-nitro-2-aza-1-propanol;
    (7) isolating the product 2-nitro-2-aza-1-propanol from the reaction mixture;
    (8) combining one mole of methylnitramine with each mole of 2-nitro-2-aza-1-propanol;
    (9) slowly adding the mixture of methylnitramine and 2-nitro-2-aza-1-propanol to concentrated sulfuric acid which is maintained at a temperature of from just above the freezing point of concentrated sulfuric acid up to 5° C.; and
    (10) isolating the product 2,4-dinitro-2,4-diazapentane.

11. The process of claim 10 wherein step (1) is performed at a temperature of from −5° C. to 0° C.

12. The process of claim 10 wherein boiling water is used in step (3).

13. The process of claim 10 wherein the molar ratio of N,N'-dimethyl-N,N'-dinitrourea to water step (3) is from 2:3 to 1:5.

14. The process of claim 10 wherein the organic solvent is selected from the group consisting of methylene chloride, chloroform, 1,2-dichloroethane, 1,1,2-trichloroethane, or mixtures thereof.

15. The process of claim 14 wherein the organic solvent is methylene chloride.

16. The process of claim 10 wherein the aqueous formaldehyde solution comprises from about 30 about 37 weight percent of formaldehyde.

17. The process of claim 10 wherein the concentrated sulfuric acid in step (5) is maintained at a temperature of from −5° C. to 0° C.

* * * * *